(12) United States Patent
Hinds et al.

(10) Patent No.: US 8,491,446 B2
(45) Date of Patent: Jul. 23, 2013

(54) EXERCISE DEVICES WITH FORCE SENSORS

(75) Inventors: Robert S. Hinds, Madison, WI (US);
Robert A. Braier, Madison, WI (US);
John Stephenson, Madison, WI (US)

(73) Assignee: Kayo Technology, Inc., Madison, WI (US)

( * ) Notice: Subject to any disclaimer, the term of this patent is extended or adjusted under 35 U.S.C. 154(b) by 0 days.

(21) Appl. No.: 13/498,012

(22) PCT Filed: Oct. 1, 2010

(86) PCT No.: PCT/US2010/051123
§ 371 (c)(1),
(2), (4) Date: Mar. 23, 2012

(87) PCT Pub. No.: WO2011/041678
PCT Pub. Date: Apr. 7, 2011

(65) Prior Publication Data
US 2012/0302406 A1    Nov. 29, 2012

Related U.S. Application Data

(60) Provisional application No. 61/248,227, filed on Oct. 2, 2009.

(51) Int. Cl.
*A63B 24/00* (2006.01)
(52) U.S. Cl.
USPC .................................... 482/8; 482/9; 482/126
(58) Field of Classification Search
USPC ........... 482/1–9, 44, 121, 122, 126, 900–902; 434/247
See application file for complete search history.

(56) References Cited

U.S. PATENT DOCUMENTS

| | | |
|---|---|---|
| D277,218 S | 1/1985 | Hinds |
| 4,779,867 A | 10/1988 | Hinds |
| 4,919,418 A | 4/1990 | Miller |
| 5,271,416 A | 12/1993 | Lepley |
| 5,505,677 A | 4/1996 | Hinds |
| 5,538,486 A | 7/1996 | France et al. |
| 5,785,632 A | 7/1998 | Greenberg et al. |
| 5,816,984 A | 10/1998 | Weiss |

(Continued)

FOREIGN PATENT DOCUMENTS

| | | |
|---|---|---|
| DE | 10350636 A1 | 6/2005 |
| EP | 1175922 A2 | 1/2002 |
| WO | WO 2008/044051 A1 | 4/2008 |

OTHER PUBLICATIONS

European Search Report Issued Mar. 8, 2013, for Application No. 10821332.3-1658/2482722 PCT/US2010051123.

*Primary Examiner* — Glenn Richman

(57) ABSTRACT

An exemplary exercise device includes a handheld force sensor with complementary male and female connectors extending from opposite sides thereof. The force sensor senses pulling and/or pushing forces exerted between the opposing sides. The male connector may be resistant to travel through the female connector except in limited orientations. The connectors allow the exercise device to interface with any mobile or immobile device having complementary connectors. Non-complementary connectors can connect with the exercise device through a body passage. Depending on devices interfaced with the exercise device, force readings can be taken during a vast variety of motions using different muscle groups during training, exercise, and rehabilitation/physical therapy in homes, schools, healthcare facilities, health clubs, etc. Force readings from the force sensor may be communicated via wired and/or wireless technologies to other devices for live (real-time) processing and display as well as additional historical analysis and reporting.

40 Claims, 5 Drawing Sheets

U.S. PATENT DOCUMENTS

| | | |
|---|---|---|
| 5,894,631 A | 4/1999 | Chiu |
| 6,093,119 A | 7/2000 | Tipton |
| 6,224,519 B1 | 5/2001 | Doolittle |
| 6,267,711 B1 | 7/2001 | Hinds |
| 6,280,361 B1 | 8/2001 | Harvey et al. |
| 6,319,179 B1 | 11/2001 | Hinds |
| 6,342,028 B1 | 1/2002 | de Sane |
| 6,398,698 B1 | 6/2002 | Hinds |
| 6,497,641 B1 | 12/2002 | Hinds |
| 6,612,170 B2 | 9/2003 | Brown |
| 6,662,651 B1 | 12/2003 | Roth |
| 6,663,544 B2 | 12/2003 | Hinds |
| 6,923,750 B1 | 8/2005 | Hinds |
| 6,941,620 B1 | 9/2005 | Hinds |
| 7,147,592 B2 | 12/2006 | Hinds et al. |
| 7,316,636 B1 | 1/2008 | Hinds et al. |
| 7,431,680 B1 | 10/2008 | Hinds et al. |
| 7,455,632 B2 | 11/2008 | Block et al. |
| 7,510,509 B2 | 3/2009 | Hickman |
| 7,682,294 B2 | 3/2010 | Piane, Jr. |
| 2002/0198081 A1 | 12/2002 | Chen |
| 2004/0176226 A1 | 9/2004 | Carlson |
| 2006/0105893 A1 | 5/2006 | Chen |
| 2007/0105696 A1 | 5/2007 | Castel et al. |
| 2008/0119763 A1 | 5/2008 | Wiener |
| 2008/0242509 A1 | 10/2008 | Menektchiev et al. |
| 2010/0197462 A1 | 8/2010 | Piane, Jr. |

EXERCISE DEVICES WITH FORCE SENSORS

CROSS-REFERENCE TO RELATED APPLICATIONS

This application claims priority under 35 USC §119(e) to U.S. Provisional Patent Application 61/248,227 filed Oct. 2, 2009, the entirety of which is incorporated by reference herein.

FIELD OF THE INVENTION

This document concerns an invention relating generally to exercise devices, and more specifically to exercise devices having force sensors for measuring, recording, and/or providing feedback regarding a user's activity.

BACKGROUND OF THE INVENTION

Force sensors are sometimes incorporated into exercise devices for monitoring user activity, e.g., the amount of force applied, the duration of exercise, etc. The force sensors can allow a user (or others, e.g., trainers or physical therapists) to quantify, record, and analyze the user's activity with greater ease and certainty. For example, a sensor might precisely measure and record the amount of weight lifted during one exercise session, as well as the number of times it was lifted, the time over which it was lifted, etc., and the recorded data can then be compared to the results of a later exercise session to determine the user's progress.

Often, the force sensors are built directly into the structures of the exercise devices. (See, e.g., U.S. Pat. Nos. 5,271,416; 6,612,170; 7,510,509; and U.S. Patent Publication 2008/0242509.) In this case, the force sensing functionality suffers from many drawbacks present in the exercise devices themselves. In particular, if the device is dedicated to the performance of only a single particular type of exercise, or a few types of exercises, the user's activity—which will often involve other types of exercise, and thus other exercise devices, as well—may not be fully captured by the force sensor. While a user might have a number of different exercise devices, each bearing its own force sensor for monitoring activities on its particular device, such an arrangement leads to greater expense, and to difficulties with collecting and organizing data from the various devices.

Some sensors are designed to be retrofit into preexisting exercise devices, as exemplified by U.S. Pat. No. 5,538,486 and U.S. Patent Publication 2008/0119763. These devices suffer from the drawback that they are not easily installed in preexisting exercise devices, and moreover tend to be installable in only a limited number and type of exercise device. They also tend to add bulk, restrict range of motion, or otherwise detract from the utility of the exercise devices.

It would therefore be useful to have available inexpensive exercise devices which are capable of accommodating a wide variety of different exercises, and which allow rapid and convenient installation and removal of force sensors for monitoring user activity, wherein the force sensors (when installed) do not interfere with the functionality and usage of the exercise devices.

SUMMARY OF THE INVENTION

Referring to FIGS. 1 and 2, an exemplary version of the exercise device includes a sensor body 100 having one or more force sensors therein (as seen at 102 in FIG. 3) or thereon, with means for connecting the sensor body 100 to other items—here illustrated as complementary male and female connectors 104 and 106 (best seen in FIG. 2)—situated on opposite sides of the sensor body 100. The force sensor(s) 102 sense pulling and/or pushing forces exerted between the two connectors 104 and 106, and communicates the measured forces to "client" devices via wireless communications (e.g., radio frequency or infrared) or wired interconnects (e.g., Universal Serial Bus interconnects) for recording, display, and/or processing. The connectors 104 and 106 allow the sensor body 100 to interface with other components having complementarily-shaped connectors, such as the elastic member 10 (which is shown having a member length 12 terminating in a member male connector 14, an arrangement which is often formed by inserting a plug within an end of an elastic tube) and the grasping loop/handle 1000 (which is shown with a loop female connector/socket 1106 which is configured to complementarily receive the member male connector 14). Looking to FIG. 1, if the elastic member 10 extends to an anchor (such as a wall or floor), and a user grips the grasping loop 1000 and pulls, on it to extend the elastic member 10, the force sensor(s) 102 between the grasping loop 1000 and the elastic member 10 detect the force exerted along the elastic member 10 between the grasping loop 1000 and the anchor. Since a wide variety of different forms of elastic members 10 are available, as well as components configured to easily connect and disconnect to such elastic members 10 (such as grasping loops 1000, bars, harnesses, etc.), the sensor body 100 can be inserted between selected elastic members 10 and components to measure the forces generated by users during exercise. Since the sensor body 100 can be readily installed and removed between many different combinations of elastic members 10 and components, a single sensor body 100 used as a standalone device (used, for example, alternatively between two or more limbs)—or two or more sensor bodies 100, one for each limb and/or other parts of the body—can be used across all (or most) of the exercises within a user's routine to capture characteristics of the user's activity. This greatly simplifies issues with data capture and calibration, since one need not compile data collected from numerous sensors having different calibration points. Further, since the sensor body 100 is easily retrofit into existing elastic member exercise devices, a user can incorporate one or more sensor bodies into his/her equipment to add force-monitoring capabilities, and can easily remove the sensor bodies if and when desired. In addition, the cost of force-monitoring exercise equipment is greatly reduced, particularly when the low cost of elastic member exercise devices is taken into account.

Referring to FIG. 2, the male connector 104 can take the form of a neck 108 extending from the sensor body 100 along a neck axis, with the neck 108 terminating in a male plug 110 having a configuration resembling that of the member male connector 14. As a result, the male plug 110 can be removably and replaceably inserted within the loop female connector 1106 of the grasping loop 1000 in the same manner as the member male connector 14. The female connector 106 can take the form of a socket body 112 having a socket passage 114 configured similarly to the loop female connector 1106 of the grasping loop 1000, and can therefore removably and replaceably receive the member male connector 14 in complementary fashion (or the male plug 110, though the male plug 110 is not ordinarily inserted within the female connector 106 during normal use). Thus, the sensor body 100 is readily installable between the elastic member 10 and the grasping loop 1000, or between any other components having complementary connections (again, with examples being noted in the patents referenced in this document).

To review the female connector 106 of FIG. 2 in greater detail, the socket body 112 includes a pair of opposing socket body sides 116 spaced by a body passage 118 extending between opposite sides of the sensor body 100. The body passage 118 may be oriented along an axis which is perpendicular to the axis of the neck 108, and also perpendicular to the length of the socket passage 114 (which is preferably parallel with the axis of the neck 108). The socket passage 114 extends between an inner socket passage end 120 opening onto the body passage 118, and an opposing outer socket passage end 122. The socket body 112 has a slot 124 opening onto the socket passage 114, with the slot 124 extending along the length of the socket passage 114 from the outer socket passage end 122 to the inner socket passage end 120 (the socket passage 114 preferably has an enlarged inner diameter which effectively defines a pocket for receiving the member male connector 14). The slot 124 is preferably sized such that male connectors 104, such as the member male connector 14 of the elastic member 10, cannot pass through the slot 124. An elastic member 10 bearing a member male connector 14 can then be easily installed into the socket passage 114 by situating the member male connector 14 in the body passage 118, and then pulling the length of the elastic member 10 along the slot 124 (while holding the member male connector 14 within the body passage 118), such that the member length 12 (whose diameter decreases with elongation) can fit through the slot 124 and into the socket passage 114. The member male connector 14 can then be released to fit within the socket passage 114 or adjacent to the inner socket passage end 120, with the length of the elastic member 10 extending from the outer socket passage end 122 (as seen in FIG. 1).

To review the male connector 104 of FIG. 2 in greater detail, the neck 108 is preferably flexible such that it will not contain any appreciable moment/bending forces during usage (e.g., if the grasping loop 1000 is rocked about the axis of the neck 108 in FIG. 1), which could distort the force measurements generated by the force sensor(s) 102. In similar respects, the plug 110 and/or neck 108 are preferably rotatable with respect to the sensor body 100, such that the neck 108 will not contain any appreciable torsional forces (e.g., if the grasping loop 1000 is rotated about the axis of the neck 108 in FIG. 1). The plug 110 may include structure which assists in firmly engaging it within a female connector, e.g., in the loop female connector 1106 of the grasping loop 1000. As an example, FIG. 2 depicts the plug 110 with a protruding longitudinal flange 126 having a length oriented parallel to the neck axis, with the longitudinal flange 126 deterring rotation of the plug 110 within the loop female connector 1106. A protruding lateral flange 128 then has a length oriented perpendicularly to the neck axis (and to the longitudinal flange 126) to resist slippage of the plug 110 through the passage of the female connector 1106.

Keeping in mind that the foregoing discussion merely summarizes features of one exemplary preferred version of the invention, further details, variations, and advantages will be apparent from the remainder of this document in conjunction with the associated drawings.

DETAILED DESCRIPTION OF PREFERRED VERSIONS OF THE INVENTION

Figure 1:
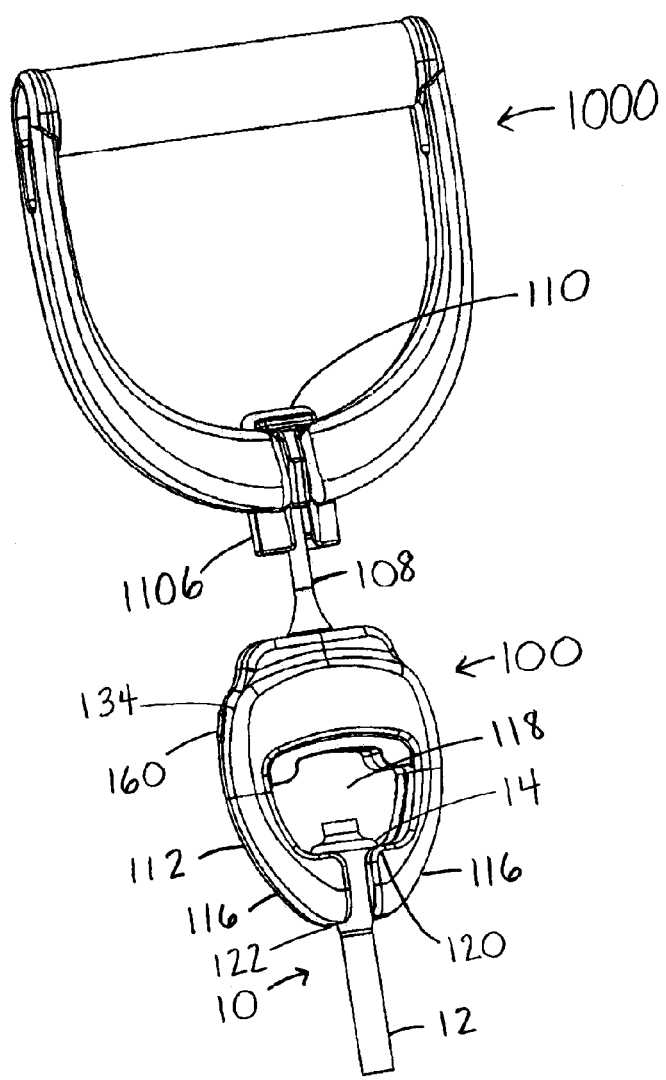
FIG. 1 shows an exemplary exercise device featuring a sensor body 100 connected to a grasping loop (handle) 1000 and elastic member 10.
Figure 2:
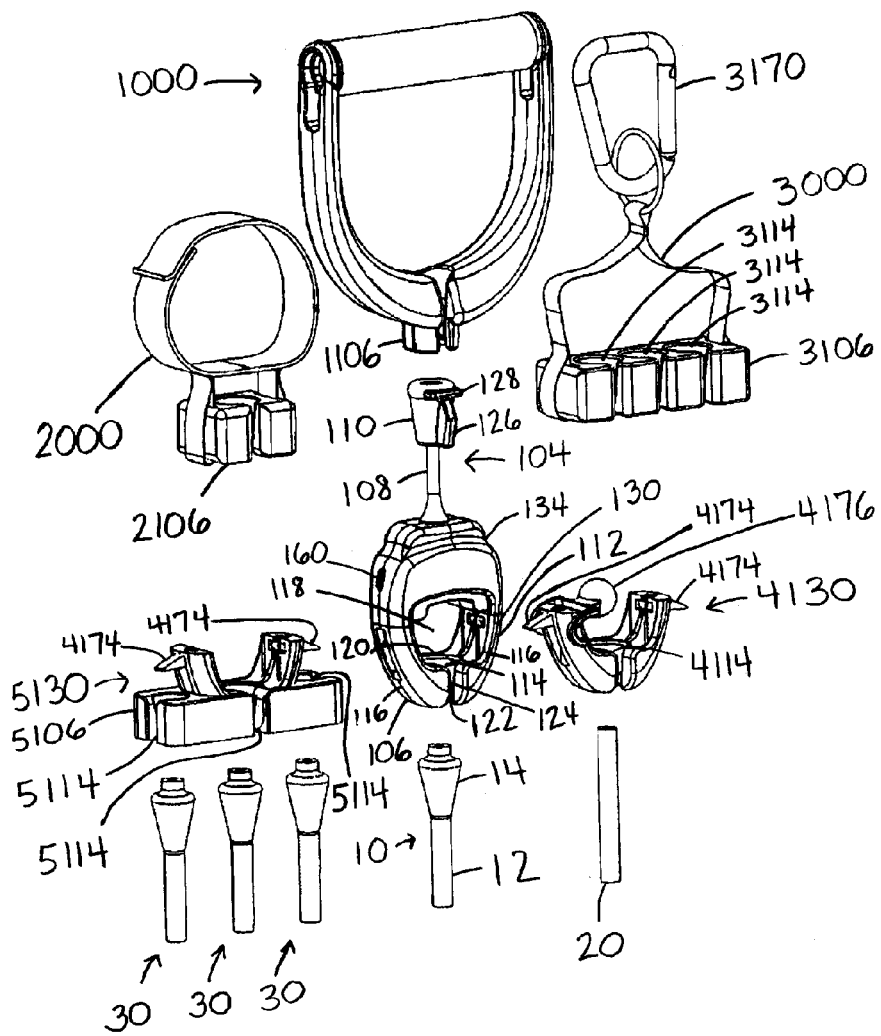
FIG. 2 shows the exercise device of FIG. 1 with the grasping loop 1000 and elastic member 10 disconnected from the sensor body 100, and with alternative components 2000, 3000, 4130, and 5130 that can be engaged with the male and female connectors 104 and 106 of the sensor body 100.
Figure 3:
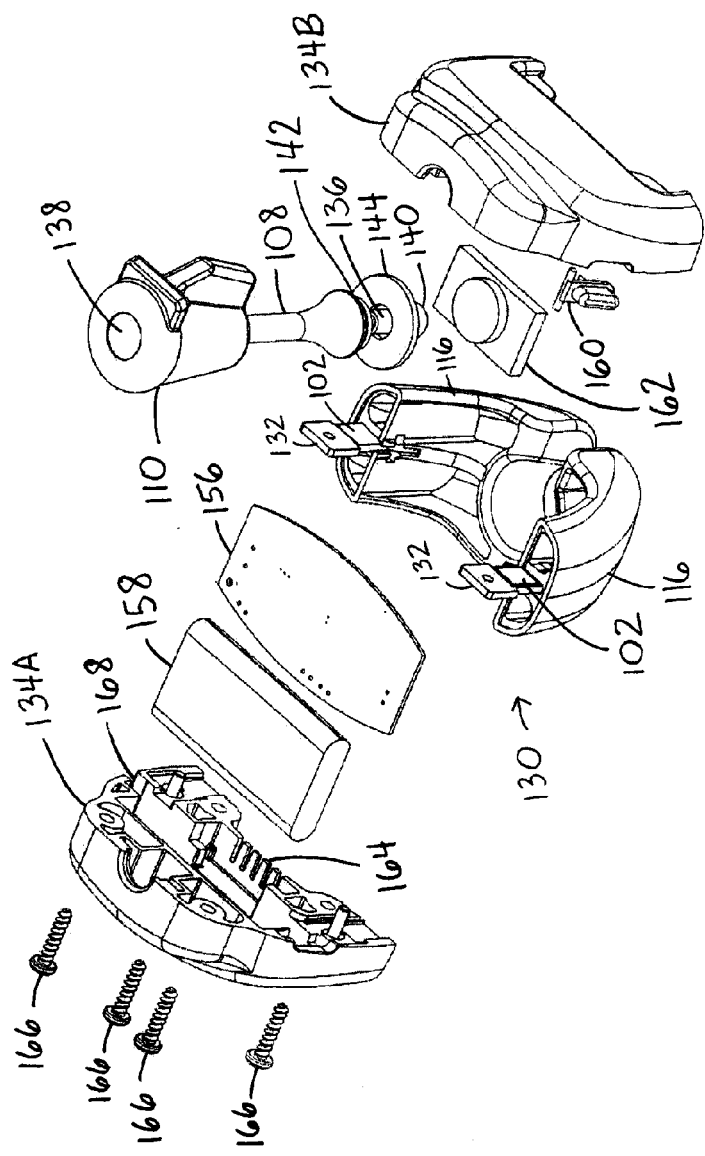
FIG. 3 shows an exploded view of the sensor body 100 of FIGS. 1 and 2.

Expanding on the discussion above, FIG. 3 illustrates an exploded (disassembled) view of the sensor body 100 of FIGS. 1 and 2. The sensor body 100 includes a female connector section 130 having bars 132 extending upwardly from the socket body sides 116, with the ends of the bars 132 being sandwiched and pinned between the depicted halves 134A and 134B of a male connector section. These bars 132 each can bear a force sensor (a load cell) 102, such that tension (or compression) between the male connector section 134A/134B and the female connector section 130—and thus on the bars 132 and the force sensors 102 thereon—results in a measurable signal representative of the force between the male and female connectors 104 and 106 of the sensor body 100.

The plug 110 and neck 108 of the male connector 104 are then shown in FIG. 3 between the halves 134A and 134B of the male connector section 134. The neck 108 is formed of a cable 136 terminating in crimped-on bosses 138 and 140, with the portion of the cable 136 extending between the male connector section 134A/134B and the plug 110 being sheathed in a flexible sleeve 142 to define the portion of the neck 108 extending from the sensor body 100 to the plug 110. One boss 138 serves to retain the plug 110 on the cable 136, and the other boss 140 serves to retain a washer-like retention ring 144 next to the end of the cable 136 situated within the male connector section 134A/134B. When the retention ring 144 is installed within and between the halves 134A and 134B of the male connector section, the plug 110 and neck 108 are firmly mounted on the sensor body 100. It is noted that while boss 140 and retention ring 144 help prevents the cable 136 of the neck 108 from being pulled out of the male connector section 134, cable 136 and/or neck 108 are preferably nonetheless rotatable with respect to the sensor body 100.

Other components depicted in FIG. 3 include a circuit board 156 which communicates with the force sensors 102, a power supply (battery) 158 which supplies power to the force sensors 102 and circuit board 156, a power button 160 for turning the aforementioned components on and off, and (optional) output devices (such as speaker 162, which rests below the circuit board 156 to emit sound through a grille 164 opening onto the body passage 118, light-emitting diodes (LEDs) or other sources of light, vibrator(s), etc.). The power button 160 may also be provided with one or more LEDs configured to indicate status or other information to the user. For example, a tricolored (RGB) LED may emit blue light when the force sensors 102 are powered on and attempting to establish a connection with a client device, green light when a connection has been established, and red light if no connection is made after a certain period of time (or if the connection is lost after it is made). Fasteners 166 are provided for fixing the halves 134A and 134B of the male connector section together. Components of the circuit board 156 are then illustrated schematically in FIG. 4 (and are discussed in greater detail below), and include an analog to digital converter (A/D converter), a power sensor, a processor (CPU), and a communications module in connection with a wireless transmitter and a wired port. FIG. 3 does not depict these components, but the half 134A of the male connector section includes an aperture 168 in which the wired port is situated (the wired port preferably taking the form of a Universal Serial Bus connector or other connector allowing communication by wire with an external device).

Figure 4:
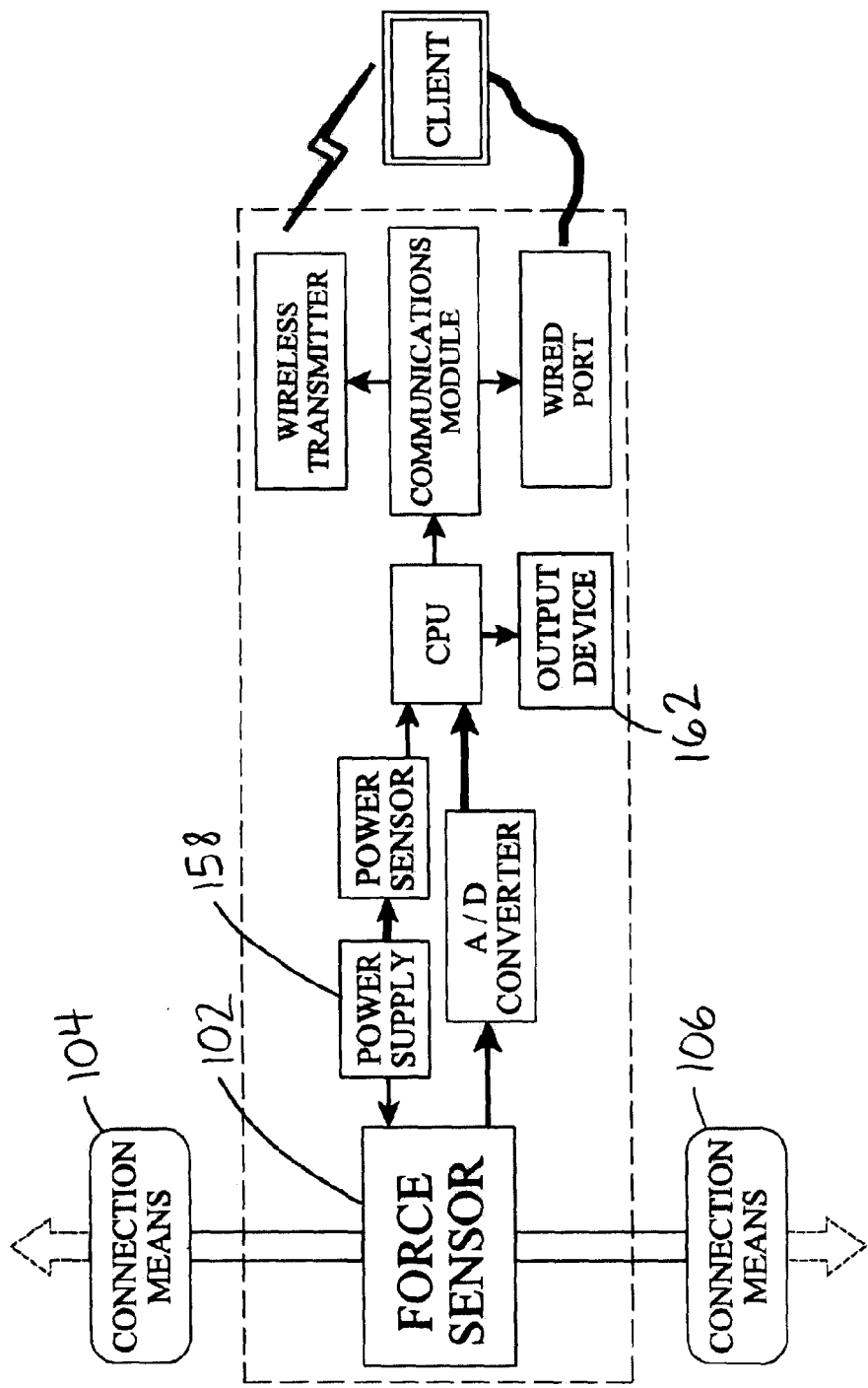
FIG. 4 schematically depicts the components and operation of the sensor body 100 of FIGS. 1-3.

Turning then to FIG. 4, the foregoing components cooperate as follows. The force sensors 102 of FIG. 3 (merely depicted as "force sensor" 102 in FIG. 4) are supplied with an input voltage from the power supply 158, and generate an output voltage dependent on the input voltage and on any force exerted on the connection means (e.g., the male and female connectors 104 and 106). The output voltage is supplied to the analog to digital converter (A/D converter), which converts the output voltage into digital form and supplies it to the processor (CPU). The processor (CPU) also receives a calibration voltage signal from a power sensor in communication with the power supply 158. This calibration voltage signal allows the processor (CPU) to determine the concurrent input voltage to the force sensor 102, such that if the voltage of the power supply 158 decreases over time, the CPU can properly scale the output voltage provided by the force sensor 102 (and the A/D converter). The CPU converts the output voltage from the force sensor 102 into a force measurement, and may also perform additional processing steps, e.g., breaking the force readings into time-stamped packets, manipulating the force readings (e.g., integrating them over time to obtain power measurements), storing a history of force readings onto an on-board memory (not shown in FIG. 4) and performing analyses on recorded readings (related to, for example, progress over time), etc. The resulting data is then provided from the CPU to the communications module, which translates the data into a transmittable signal for communication to a "client" device via a wireless transmitter and/or via a wired port (with details of these devices being discussed below).

The client device illustrated in FIG. 4 may take the form of one or more of a variety of devices which are capable of storing, displaying, and/or transmitting the data from the sensor body 100, including personal computers, mobile devices (such as mobile telephones like IPHONE manufactured by Apple Inc. of Cupertino, Calif., USA, personal digital assistants, handheld computers like IPAD manufactured by Apple Inc., and multimedia devices like IPOD manufactured by Apple Inc.), and game consoles (such as a PLAYSTATION console manufactured by the Sony Corporation of Tokyo, Japan, a NINTENDO console manufactured by Nintendo Co., Ltd., of Kyoto, Japan, or an XBOX console manufactured by the Microsoft Corporation of Redmond, Wash., USA). These are merely preferred client devices, and a wide variety of other clients are also possible, e.g., various types of monitors/displays (such as digitally-enabled televisions), web-based applications (accessible via net-enabled devices), wearable devices (such as sport watches and ankle bracelets), etc. The ability to supply data to mobile telephones and other mobile devices is particularly useful since this allows a user to readily store and transport both a data capture device (i.e., the sensor body 100) and a data review device (i.e., the mobile device and its associated visual and/or audio output components). In this respect, it is notable that the sensor body 100 might transmit exercise data to a web application, and the user might then be able to direct the browser of his/her mobile device to the web application, or call in to the web application, to obtain a visual and/or audio presentation of the data.

The client device may then perform data recordation, audiovisual feedback, and other functionality, such as displaying live (real-time) force values in graphical form; tracking progress of the user and his/her exercise routine; indicating milestone force values using audiovisual cues; providing long-term data storage; reporting real-time and historical (or cumulative) data trends, calculations, and analyses; instructing users on proper exercise techniques and recommended exercise routines; providing a user interface allowing for the specification and adjustment of workout parameters, alarms, routines, etc.; and correlating data from the sensor body 100 with data from other devices, e.g., heart monitors or other physiological sensors. It is possible to change the configuration of the sensor body 100 to perform some or all of these functions as well, e.g., by incorporating input and output devices (see, e.g., FIG. 4) into the sensor body 100 (such as input buttons/scroll wheels, an LCD display screen, a bank of LED lights, etc.), but it is preferred to restrict the functionality of the sensor body 100 to (primarily) the collection of force data, with most other functions being moved to a separate client device. This arrangement reduces the cost, complexity, and fragility of the sensor body 100, and also allows for easier upgrades in functionality because the client device might be reprogrammed or replaced as needed to provide desired functionality.

Where audiovisual feedback of force measurements (or other information) is provided, it can be supplied by, for example, the aforementioned speaker 162 of FIG. 3, LEDs or other sources of light, and/or LCD displays, as well as (or instead of) by a client device. Most preferably, the processor (CPU) of FIG. 4 is configured such that it can provide output via one or more output devices (such as the speaker 162 outputting sounds and/or voices, light sources, vibrators, etc.) in circumstances where no client device is available via wireless or wired communications and the sensor body 100 is made usable by itself as a standalone device. In this case, various audio messages can be associated with different information or events, with (for example) a first sound indicating that the measured force has met or exceeded a target force level, or a maximum force limit; a second sound signalling the time for which a pose or a motion should be sustained ("hold time"); a third sound if the measured force falls below the relaxation force for a given repetition; a fourth sound indicating the completion of an exercise, or the completion of an entire workout routine, or the attainment of a workout milestone (for example, total calories burned, total work done, etc.); and so forth. Audio cues in user-selected languages (as well as visual and/or tactile cues using various output devices) can provide instructions on (for example) how to perform various exercises, to move in various directions, or to use different muscles. Sound can also be used to provide rhythmic output, like that of a metronome, to assist with user timing of actions. Usefully, audio feedback permits a user to obtain feedback without needing to face and view a display.

Regarding the aforementioned possibility of using the sensor body 100 where no client device is available, it can be useful for the sensor body 100 to include sufficient onboard memory that it can store the results of at least one of the user's exercise sessions for later downloading/transmission. In this respect, if a removable memory is desired, the location of the wired port might be changed (if necessary) from that shown at 168 in FIG. 3 to, for example, the body passage 118, so that a removable memory device might be more securely affixed to the sensor body 100 in a non-protruding and relatively sheltered location. In similar respects, a removable display or the like (e.g., a small LCD display) might be installed on the sensor body 100 via a wired port situated at an appropriate location (though it is preferred that the sensor body 100 omit such components for the sake of durability, compactness, and being light weight).

Turning back to FIGS. 1 and 2, it should be understood that the sensor body 100 may be interposed between a wide variety of components other than the grasping loop 1000 and the elastic member 10. FIG. 2 illustrates a variety of components which can be attached to the male connector 104 in lieu of the rigid grasping loop 1000. A flexible belt-like grasping loop 2000 suitable for attachment about a wrist or ankle is shown connected to a female connector 2106 for receiving an elastic member 10, or for receiving the plug 110 of the male connector 104. Grasping loops can assume forms other than those provided by the grasping loops 1000 and 2000, and can include any rigid and/or flexible loop which is able to engage, or be engaged by, a part of the user's body, such as a handle loop which can be grasped by the user's hand, a stirrup that can be engaged by a user's foot, or a loop which can be engaged about a user's wrist, ankle, waist, head, neck, torso, etc. FIG. 2 also illustrates a female connector 3106 having three socket passages 3114, any one or more of which can receive an elastic member 10 or the plug 110, and it carries a strap 3000 bearing a carabiner 3170 (for attachment to a user's belt, to a suspended bar, a ring anchored to a wall or floor, etc.). Other components for attachment to the male connector 104 are also possible, including simply a structure which bears a female socket configured to complementarily receive the male plug 110, and which is anchored to a floor, wall, or other surroundings. The attachment of the foregoing and other components to the sensor body 100 can occur at the female connector 106 instead of (or in addition to) at the male connector 104, as by providing the components 1000, 2000, and 3000 with male plugs similar to plug 110 rather than female connectors, and engaging them within the socket passage 114 of the female connector 106.

Figure 5:
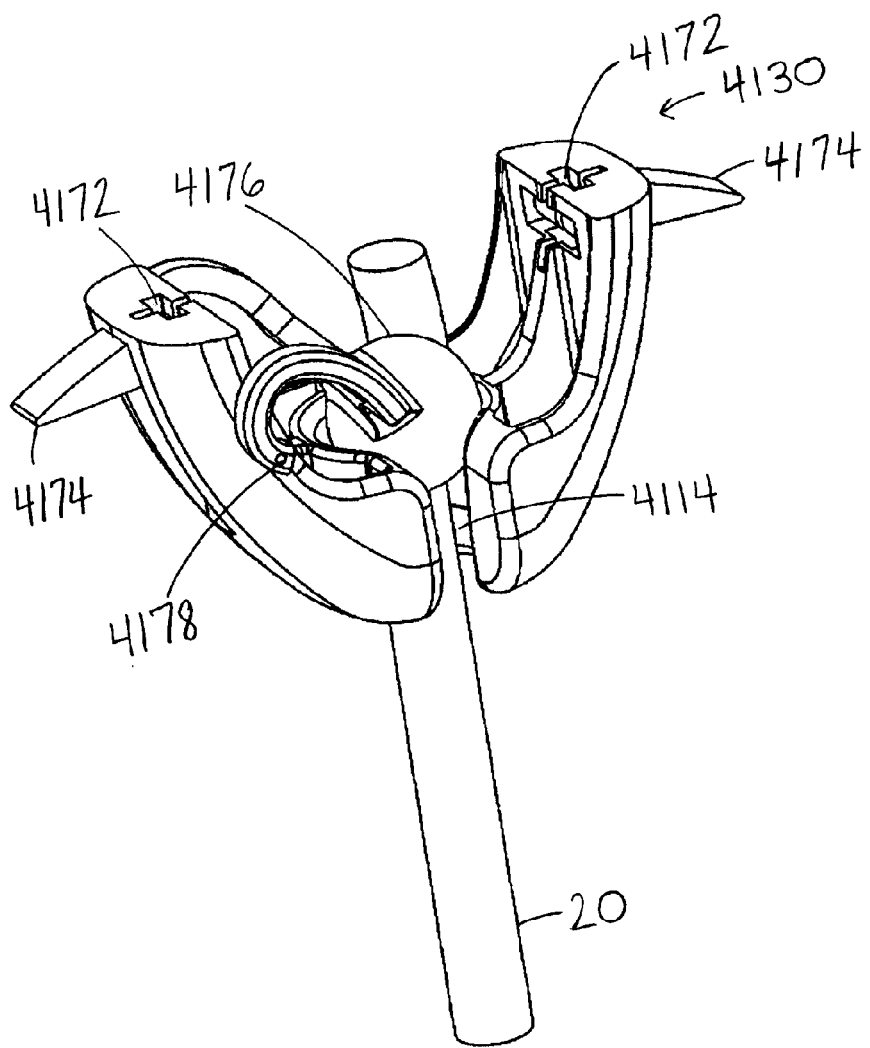
FIG. 5 provides a more detailed view of the female connector section 4130 of FIG. 2.

FIG. 2 also illustrates a possible arrangement wherein a variety of female connector sections 130, 4130, and 5130 are provided, each having a different form of connection means for attachment to elastic members 10/20/30 or other structures. The female connector sections 130, 4130, and 5130 may be interchangeably installable and removable on the male connector section 134, such as by using latches 4174 as discussed below for female connector section 4130. Initially refer to the female connector section 4130, which is illustrated in greater detail in FIG. 5. This female connector section 4130 is configured generally similarly to the female connector section 130 shown in FIGS. 1-3, but contemplates that the force sensor-bearing bars 132 seen in FIG. 3 protrude from the male connector section 134 rather than the female connector section 4130 to be received and pinned (or otherwise engaged) within the female connector section 4130. The female connector section 4130 bears slots 4172 for receiving the bars 132, and latches 4174 are pivotally connected to the female connector section 4130 near the slots 4172. The latches 4174 can be urged from the disengaged position shown in FIG. 5 to an engaged position (not shown) wherein pins or other structure (not shown) provided on or in connection with the latches 4174 engage the bars 132 to fix the male connector section 134 to the female connector section 4130. The female connector section 4130 also differs from the female connector section 130 in that it has a bearing member 4176 pivotally affixed at hinges 4178 such that it may move between a bearing position situated along the path of the socket passage 4114, and a non-bearing position situated outside (or to a lesser extent within) the path of the socket passage 4114. In the bearing position, the bearing member 4176 is able to bear against any elastic member 20 extending through the socket passage 4114, and the bearing member 4176 is pivotally mounted with respect to the female connector section 4130 such that any attempt to withdraw the elastic member 20 from the socket passage 4114 (i.e., downwardly in FIG. 5) will tend to pull the bearing member 4176 into the socket passage 4114, thereby more tightly bearing against the elastic member 20. This arrangement is useful when the elastic member 20 lacks a member male connector (as shown in FIG. 5), or when one wishes to adjust the length of the elastic member 20 extending through the socket passage 4114, since the elastic member 20 may be extended through the socket passage 4114 to a desired extent, and the bearing member 4176 may then be urged against the elastic member 20 to fix it within the socket passage 4114. When desired, the bearing member 4176 may be moved to the non-bearing position to disengage the elastic member 20 to allow the elastic member 20 to freely travel through the socket passage 4114.

FIG. 2 also illustrates a female connector section 5130 which resembles the female connector section 4130 of FIG. 5, except it bears a female connector 5106 resembling the female connector 3106 shown at the upper right-hand side of FIG. 2, with three socket passages 5114 that allow installation of one to three elastic members 30.

Preferred versions of the invention have been reviewed in the foregoing discussion to illustrate different possible features of the invention and the varying ways in which these features may be combined. Apart from combining the different features of the foregoing versions in varying ways, other modifications are also considered to be within the scope of the invention. Following is an exemplary list of such modifications.

Initially, it must be kept in mind that the exercise devices and sensor body 100 shown in the accompanying drawings and discussed above are merely exemplary, and may assume a wide variety of configurations different from those noted, and may use components different from those noted. Regarding components, the force sensor 102 may take the form of single or multiple sensors, and need not take the form of a load cell. As examples, piezoelectric sensors, accelerometers, linear variable differential transformers (LVDTs), or any multi-axis sensors capable of measuring quantities such as torque, bending, stretching, pressure, etc. where desired, and/or other sensors may be used instead of or in addition to load cells. The wireless transmitter can take the form of a radio frequency transmitter (e.g., WiFi, Bluetooth, ANT, ANT+, ZigBee, etc.), an optical transmitter (e.g., an infrared transmitter), an ultrasonic transmitter, or the like. The wired port can take the form of an Ethernet port, a serial port, a parallel port, an IEEE 1394 interface (a "FireWire" port), or any other known connector suitable for allowing wired transmission of data.

The power supply 158, while preferably taking the form of a rechargeable battery (which might be charged via the wired port or another connector), could instead be a replaceable battery, or might even be omitted in lieu of power supply via a wired connection (again via the wired port or another connector). The device may also be partly or entirely powered by converting pulling and/or pushing forces into energy that can power its components. That is, the energy expended while using the device could be harvested, such that kinetic energy is transduced into electrical and/or chemical energy that can be used to power its various parts and/or otherwise stored for later use (such as by recharging a battery). This can be accomplished by any suitable means available, such as by incorporating piezoelectric crystals that generate voltage when mechanically deformed, or through the movement of magnets in an electromagnetic generator (caused by movements of the device) providing a rate of change of magnetic flux and inducing an electromagnetic field (EMF) on the coils.

As noted previously, the female connector section 5130 of FIG. 2 may be used if it is desirable to attach one or more male members to the sensor body 100. In similar respects, the male connector section 134 might bear more than one male connector 104, e.g., more than one neck 108 and plug 110. It is also possible that different sides of the sensor body 100 can bear different combinations of one or more male and/or female connectors 104 and 106. As an example, the sensor body 100 might bear a male connector 104 extending along one axis, and multiple female connectors 106 spaced from the male connector 104 about the sensor body 100 (and the connectors 104/106 need not be situated along a common plane).

The male connector 104 need not take the form of a flexible neck 108, and the neck 108 could be rigid instead. Such an arrangement is useful in situations where the sensor body 100 might be used to monitor forces subjecting the sensor body 100 to compression rather than tension. The neck 108 might also be extensible and retractable with respect to the sensor body 100, such that when the plug 110 and neck 108 are installed in a loop female connector 1106 (as in FIG. 1), the neck 108 might be withdrawn into the sensor body 100 such that the female connector 1106 is tightly sandwiched between the plug 110 and the sensor body 100. A simple way to attain such an arrangement is to provide the neck 108 as a threaded shaft which can be rotated to retract and extend it with respect to the sensor body 100. As an alternative, the neck 108 could be defined by a shaft bearing a protruding boss near its end opposite the plug 110, with the boss sliding within a keyway in the sensor body 100 as the neck 108 is pushed into a passage within the sensor body 100. An annular groove might then be defined about the passage at a certain depth therein, such that when the boss encounters the groove, the shaft can be rotated to move the boss out of the keyway and into the groove, preventing withdrawal of the shaft/neck 108 until the boss is rotated back into the keyway. Other retractable neck arrangements will be apparent to an ordinarily skilled designer.

More generally, the connection means need not take the form of a plug 110 and neck 108 and/or a female passage 114, and can be any structure suitable for attaching the sensor body 100 to an elastic member 10, to an anchor (i.e., a relatively immovable structure), or to components such as grasping loops 1000. As an example, looking to FIG. 2, the depicted male connector 104 or female connector 106 might be replaced with a strap, cord, chain, or other flexible member which can be tied or otherwise affixed to an anchor or other structure (with the male connector section 134 or female connector section 130 bearing a buckle, ring, insertion passage, or other structure for attaching such flexible members). Alternatively, the depicted male connector 104 or female connector 106 might be replaced with a ring, carabiner, hook, clamp, or other structure allowing attachment to an anchor or other structure (either directly or indirectly, for example, via an intermediate elastic member 10). As an illustration, in FIG. 2, the strap 3000 of the female connector 3106 might be directly mounted to the male connector section 134 so that the carabiner 3170 defines the connection means thereon. The reader is referred to the patents and other publications noted in this document for examples of other forms of connection means that might be used.

It is noted that other components and/or devices need not have complementary male and/or female connectors to interface with the exercise device. Other components may have members that are able to enter through the body passage 118 to connect to the exercise device. For example, a cord, rope, chain, flat band, etc., can enter the body passage 118 and loop around the socket body 112, socket body sides 116, and/or the male connector section 134 and be tied to itself (via a knot) or otherwise attached to the exercise device. Alternatively or additionally, one or more rings, hooks, etc. (such as carabiner 3170) can be used to hook onto, for example, one or more socket body sides 116. The force sensor 102 would then be able to measure force exerted between, for example, a grasping loop and a member so attached. This greatly enhances the versatility, convenience, and usability of the exercise device by allowing it to interact with and engage even more types of components and devices.

As another exemplary variation, the grasping loops 1000/2000 of FIG. 2 (or other forms of grasping loops) could be joined directly (e.g., by welding) or indirectly (e.g., via webbing or other connection means) to the male connector section 134 or the female connector section 130. The other connector section could then be connected to an elastic member 10, an anchor, or another structure, whereby a user can grasp (or be grasped by) the grasping loop to exert force on the sensor body 100.

The body passage 118 extending between opposite sides of the sensor body 100 might have one side blocked by a barrier. For example, the side of the exercise device opposite the side with the slot 124 can include a wall extending from the sensor body 100 to the inner socket passage end 120, and extending between socket body sides 116. This would provide a confined space via which the socket passage 114 can be accessed by a male connector. Alternatively, the exercise device need not be provided with a body passage, in which case the sensor body 100 might be continuous with the socket body 112.

While the foregoing discussion has generally spoken of the use of grasping loops 1000 for gripping by a user (or gripping of a user) to act on the sensor body 100, other forms of grips—e.g., a simple bar with an elastic member 10 mounted to its length—can be used instead.

The bearing member 4176 of FIGS. 3 and 5 is not restricted to the depicted ball-like form, and may take the form of a tongue, hook, or any other structure capable of impeding the socket passage 4114 and/or pressing against an elastic member 20. Further, the bearing member 4176 may move between bearing and non-bearing positions by other than pivotal motion, e.g., a bearing member 4176 might additionally or alternatively translate within the path of the socket passage 4114. Examples of additional or alternative bearing members include those found in U.S. Pat. Nos. 6,398,698; 6,663,544; 7,147,592; and 7,316,636.

Finally, while this document has generally discussed the use of elastic members in the form of elastic tubes with embedded plugs defining male connectors, it should be understood that other forms of elastic members can be used instead, e.g., elastic tubes without male connectors (such as the one in FIG. 5), elastic cords, elastic straps, springs (made of, e.g., steel or other materials), or the like. Where no member male connector (such as the member male connector 14 of FIG. 2) is present, these can be used in conjunction with a female connector 106 having a bearing member 4176 (as in FIG. 2), or they could simply be inserted through a socket passage 114 of a female connector 106 and then tied about the female connector 106, or they could be knotted to prevent their travel through the socket passage 114, to engage them to the sensor body 100. Further, the invention could utilize inelastic members rather than elastic members—e.g., inelastic cords/cables, chains, straps, and the like—with the inelastic members being installed in generally the same manner as the aforementioned elastic members.

Prior patents and other documents noted in the foregoing discussion should be regarded as incorporated by reference, such that the contents of these documents also effectively define contents of this document.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. An exercise device including:
   a) an elastic member having a member male connector thereon;
   b) a grasping loop having a loop female connector thereon, the loop female connector being configured to removably and replaceably receive the member male connector in complementary fashion, whereby the grasping loop can be installed on the elastic member to allow a user to act on the grasping loop to stretch the elastic member; and
   c) a sensor body having:
      1) a force sensor;
      2) a sensor body male connector configured to be removably and replaceably received within the loop female connector in complementary fashion, whereby the grasping loop can be installed on the sensor body to allow a user to act on the grasping loop to exert force on the sensor body; and
      3) a sensor body female connector configured to removably and replaceably receive the member male connector in complementary fashion, whereby the sensor body can be installed on the elastic member to allow a user to act on the elastic member to exert force on the sensor body;
   the sensor body being removably and replaceably installable between the grasping loop and elastic member, whereby the force sensor senses force exerted between the grasping loop and the elastic member.

2. The exercise device of claim 1 wherein:
   a) the sensor body is connected to an anchor via the sensor body female connector, and
   b) the force sensor senses force exerted between the anchor and the grasping loop.

3. The exercise device of claim 1 wherein the sensor body female connector:
   a) defines a terminal end of the sensor body, and
   b) is removable and replaceable from the sensor body.

4. The exercise device of claim 1 wherein:
   a) the sensor body male connector includes a neck extending from the sensor body, the neck terminating in a male plug, and
   b) the sensor body female connector is configured to removably and replaceably receive the male plug in complementary fashion.

5. The exercise device of claim 4 wherein the neck is flexible.

6. The exercise device of claim 4 wherein the male plug is rotatable with respect to the sensor body.

7. The exercise device of claim 4 wherein the male plug is configured with a nonuniform circumference such that when it is complementarily received within the loop female connector, it cannot rotate therein.

8. The exercise device of claim 1 wherein:
   a) the sensor body female connector further includes a socket passage configured to removably and replaceably receive the member male connector in complementary fashion,
   b) the socket passage includes a slot opening thereon, the slot:
      1) extending along the length of the socket passage, and
      2) being configured to inhibit the member male connector from entering the socket passage through the slot.

9. The exercise device of claim 8 wherein:
   a) the socket passage extends between an inner socket passage end and an opposing outer socket passage end, and
   b) the inner socket passage end opens onto a body passage:
      1) extending along an axis which is perpendicular to the length of the socket passage, and
      2) having a diameter greater than the diameter of the socket passage.

10. The exercise device of claim 8 further including a bearing member movably affixed to the sensor body, the bearing member being movable between:
   a) a bearing position adjacent to the socket passage, wherein the bearing member may bear against any elastic member extending through the socket passage to inhibit the elastic member from being pulled through the socket passage, and
   b) a non-bearing position spaced from the bearing position.

11. The exercise device of claim 1 wherein:
   a) the sensor body male connector includes a neck extending from the sensor body, the neck terminating in a male plug, and
   b) the neck is retractable with respect to the sensor body such that the distance between the sensor body and the male plug is adjustable.

12. The exercise device of claim 1 wherein:
   a) the sensor body male connector includes an elongated neck extending from the sensor body along a neck axis, and
   b) the sensor body includes two force sensors therein, the force sensors being situated on opposite sides of the neck axis between the sensor body female connector and the neck.

13. An exercise device including:
   a) a sensor body having a force sensor;
   b) a neck having a length extending from the sensor body, the neck having a male plug situated thereon spaced from the sensor body, with the male plug having portions extending outwardly from the circumference of the neck; and
   c) a socket body spaced from the neck wherein:
      1) the force sensor is situated between the male plug and the socket body, whereby the force sensor senses force exerted between the male plug and the socket body; and
      2) the socket body is defined by a socket passage configured such that the socket passage can receive the neck therein, but prohibits passage of the male plug through the socket passage, whereby the male plug prevents pulling of the neck and male plug through the socket passage.

14. The exercise device of claim 13 wherein:
   a) the socket body is connected to an anchor via one of the socket passage and the male plug of the neck, and
   b) the force sensor senses force exerted between the anchor and the socket body.

15. The exercise device of claim 14 wherein the neck is flexible.

16. The exercise device of claim 15 wherein the male plug is rotatable with respect to the neck.

17. The exercise device of claim 14 wherein the socket body:
   a) defines a terminal end of the sensor body, and
   b) is removably and replaceably affixed to the sensor body.

18. The exercise device of claim 13 wherein the neck is retractable with respect to the sensor body, such that the distance between the sensor body and the male plug is adjustable.

19. The exercise device of claim 13 wherein the socket passage:
   a) extends between opposing socket passage ends, and
   b) includes a slot extending between the opposing socket passage ends and opening onto the socket passage.

20. The exercise device of claim 13 wherein the exercise device further includes a bearing member movably affixed to at least one of the socket body and the sensor body, the bearing member being movable between:
   a) a bearing position adjacent to the socket passage, and
   b) a non-bearing position spaced from the bearing position.

21. The exercise device of claim 13 wherein the socket body includes a pair of opposing socket body sides extending from the sensor body, with a body passage:
   a) defined between the socket body sides, and
   b) extending between opposite first and second faces of the exercise device from an intermediate face defined at an end of the socket body.

22. The exercise device of claim 13 wherein the outwardly extending portions of the male plug include a longitudinal flange having a length oriented at least substantially parallel with the length of the neck.

23. The exercise device of claim 22 wherein the outwardly extending portions of the male plug further include a lateral flange having a length oriented at least substantially perpendicular to the length of the neck.

24. The exercise device of claim 13 further including an elastic member having a member male connector thereon, wherein the member male connector is:
   a) removably insertable within the socket passage, and
   b) configured such that it cannot be pulled through the socket passage.

25. The exercise device of claim 24 further including a grasping loop having a loop female connector thereon, wherein:
   a) the male plug of the neck is removably insertable within the loop female connector, and
   b) the force sensor senses force exerted between the elastic member and the grasping loop.

26. An exercise device including:
   a) a sensor body having a force sensor;
   b) a socket body on the sensor body, the socket body having:
      1) opposing socket body sides spaced by a body passage extending between opposite first and second faces of the socket body;
      2) a socket passage:
         (i) extending from an intermediate face of the socket body:
            A. defined at an end of the socket body, and
            B. situated between the first and second faces;
         (ii) extending through the socket body between the socket body sides, and
         (ii) opening onto the body passage,
         wherein the socket passage is configured to have an elongated elastic member secured therein; and
   c) connection means for connecting the sensor body to an anchor, wherein the force sensor senses force exerted between the socket body and the connection means.

27. The exercise device of claim 26 wherein the socket body is removably and replaceably affixed to the sensor body.

28. The exercise device of claim 26 wherein the connection means includes a neck terminating in a male plug, the male plug configured to be removably and replaceably receivable within the socket passage in complementary fashion.

29. The exercise device of claim 28 wherein:
   a) the neck is flexible, and
   b) the male plug is rotatable with respect to the sensor body.

30. The exercise device of claim 29 wherein the male plug is configured with a nonuniform circumference such that it is not rotatable with respect to the anchor when connected thereto.

31. The exercise device of claim 26 wherein:
   a) the sensor body further includes a neck terminating in a male plug, and
   b) the neck is retractable, such that the distance between the male plug and the sensor body is adjustable.

32. The exercise device of claim 26 further including an elastic member having a member male connector thereon, wherein the member male connector is configured to be removably and replaceably receivable in complementary fashion within the socket passage such that it cannot be pulled through the socket passage when situated therein.

33. The exercise device of claim 32 further including a bearing member movably affixed to at least one of the socket body and the sensor body, the bearing member being movable between:
   a) a bearing position adjacent to the socket passage, the bearing member being configured to inhibit the elastic member from being pulled through the socket passage when in the bearing position, and
   b) a non-bearing position spaced from the bearing position.

34. The exercise device of claim 32 further including a grasping loop having a loop female connector thereon, wherein:
   a) the male plug is removably receivable within the loop female connector in complementary fashion, and
   b) the force sensor senses force exerted between the elastic member and the grasping loop.

35. An exercise device including:
   a) a sensor body having:
      1) a force sensor, and
      2) a sensor body first end and an opposing sensor body second end;
   b) a neck affixed to the sensor body first end, the neck:
      1) extending from the sensor body along a neck axis, and
      2) terminating in a male plug;
   c) a socket body affixed to the sensor body second end, the socket body:
      1) being situated along the neck axis, and
      2) including a socket passage having a shape complementary to the shape of the male plug, the socket passage being configured:
         (i) to removably and replaceably receive the male plug, and
         (ii) to restrict the male plug from passage through the socket passage along the long axis;
      wherein the force sensor is configured to sense force exerted between the neck and the socket passage.

36. The exercise device of claim 35 wherein the male plug includes:
   a) a lateral flange configured to prevent the male plug from passing through the socket passage along the neck axis, and
   b) a longitudinal flange configured to prevent the male plug from rotating within the socket passage.

37. The exercise device of claim 36, wherein
a) the socket body has a body passage extending therethrough between opposite faces of the exercise device,
b) the socket passage:
   1) extends between opposing socket passage ends, wherein one of the socket passage ends opens onto the body passage and the other of the socket passage ends opens onto an end of the socket body; and
   2) includes a slot opening onto the socket passage,
c) the exercise device further includes:
   1) an elastic member having a member male connector thereon, the member male connector being complementarily receivable within the socket passage; and
   2) a grasping loop having a loop female connector thereon, the male plug of the neck being complementarily receivable within the loop female connector, and
d) the force sensor senses force exerted between the grasping loop and the elastic member.

38. The exercise device of claim 35 wherein:
a) the neck is flexible, and
b) the male plug is rotatable about the neck axis with respect to the sensor body.

39. The exercise device of claim 35 wherein the socket body:
a) is situated at a terminal end of the sensor body, and
b) is replaceably removable from the sensor body.

40. The exercise device of claim 35 wherein:
a) the socket body is removably connected to an anchor, and
b) the force sensor senses force exerted between the anchor and the socket body.

* * * * *